United States Patent
Weerakoon et al.

(10) Patent No.: US 10,426,935 B2
(45) Date of Patent: Oct. 1, 2019

(54) REINFORCED SYRINGE BODY

(71) Applicant: Merit Medical Systems, Inc., South Jordan, UT (US)

(72) Inventors: Prasad Weerakoon, Provo, UT (US); Jon Davis, Sandy, UT (US); Russell D. Heyborne, Riverton, UT (US); Larry T. Wilde, Hyrum, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 229 days.

(21) Appl. No.: 15/202,785

(22) Filed: Jul. 6, 2016

(65) Prior Publication Data

US 2017/0007807 A1    Jan. 12, 2017

Related U.S. Application Data

(60) Provisional application No. 62/188,982, filed on Jul. 6, 2015.

(51) Int. Cl.
*A61M 25/10* (2013.01)

(52) U.S. Cl.
CPC .............................. *A61M 25/10182* (2013.11)

(58) Field of Classification Search
CPC .......... A61M 5/3202; A61M 25/10182; A61M 1/3653; A61M 1/3661; A61M 2005/3121; A61M 2016/0027; A61M 5/3137; A61M 5/3275; A61M 25/0023; A61M 25/0032; A61M 25/10188; A61M 5/2429; A61M 2005/3206; A61M 2205/3331; A61M 5/3243; A61M 5/347; A61M 2005/3104; A61M 2205/073; A61M 5/30

USPC ........ 604/6.16, 43, 68, 70, 71, 72, 140, 195, 604/246, 257, 258, 264, 272, 275, 311

See application file for complete search history.

(56) References Cited

U.S. PATENT DOCUMENTS

| 3,901,413 | A | * | 8/1975 | Harris, Sr. | .............. | B01L 3/022 |
| | | | | | | 222/309 |
| 4,929,238 | A | * | 5/1990 | Baum | ............. | A61M 25/10182 |
| | | | | | | 604/118 |
| 4,966,581 | A | * | 10/1990 | Landau | ................... | A61M 5/30 |
| | | | | | | 604/244 |
| 5,205,823 | A | | 4/1993 | Zdeb | | |
| 5,814,917 | A | * | 9/1998 | Isobe | ................. | H03H 9/14538 |
| | | | | | | 310/313 B |

(Continued)

FOREIGN PATENT DOCUMENTS

| EP | 1602389 | 12/2005 |
| WO | 200041494 | 7/2000 |
| WO | 2014077670 | 5/2014 |

OTHER PUBLICATIONS

International Search Report and Written Opinion dated Oct. 20, 2016 for PCT/US2016/041047.

*Primary Examiner* — Brandy S Lee
(74) *Attorney, Agent, or Firm* — Stoel Rives LLP

(57) ABSTRACT

A syringe body is disclosed, wherein the syringe body is configured to withstand pressures within a fluid reservoir of the syringe body of between about 0 atmospheres (atm) and about 81 atm and/or between about 0 atm and about 109 atm. The syringe body may be configured for use in connection with an inflation device. The syringe body may comprise one or more stiffening ribs and/or a stiffening lip. Methods of using the syringe body in connection with an inflation device are also disclosed.

15 Claims, 13 Drawing Sheets

(56) References Cited

U.S. PATENT DOCUMENTS

| | | | |
|---|---|---|---|
| 6,203,521 B1* | 3/2001 | Menne | A61M 5/30 604/140 |
| 7,022,112 B2* | 4/2006 | Pokorney | A61M 5/31511 604/227 |
| 7,604,618 B2* | 10/2009 | Dixon | A61B 17/8822 604/122 |
| 9,332,972 B2* | 5/2016 | Boutaghou | A61B 10/0283 |
| 2010/0168662 A1* | 7/2010 | Bingham | A61M 5/30 604/68 |
| 2014/0100509 A1 | 4/2014 | Defonzo | |
| 2014/0288509 A1* | 9/2014 | Altmeyer | A61M 5/31513 604/222 |

* cited by examiner

REINFORCED SYRINGE BODY

RELATED APPLICATIONS

This application claims priority to U.S. Provisional Application No. 62/188,982, filed on Jul. 6, 2015 and titled, "Reinforced Syringe Body," which is hereby incorporated by reference in its entirety.

TECHNICAL FIELD

The present disclosure relates generally to syringe bodies for use with inflation devices. More specifically, the present disclosure relates to reinforced syringe bodies configured for use with devices used to pressurize, depressurize, or otherwise displace fluid along a line in order to inflate or deflate a medical device such as a balloon.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1A:
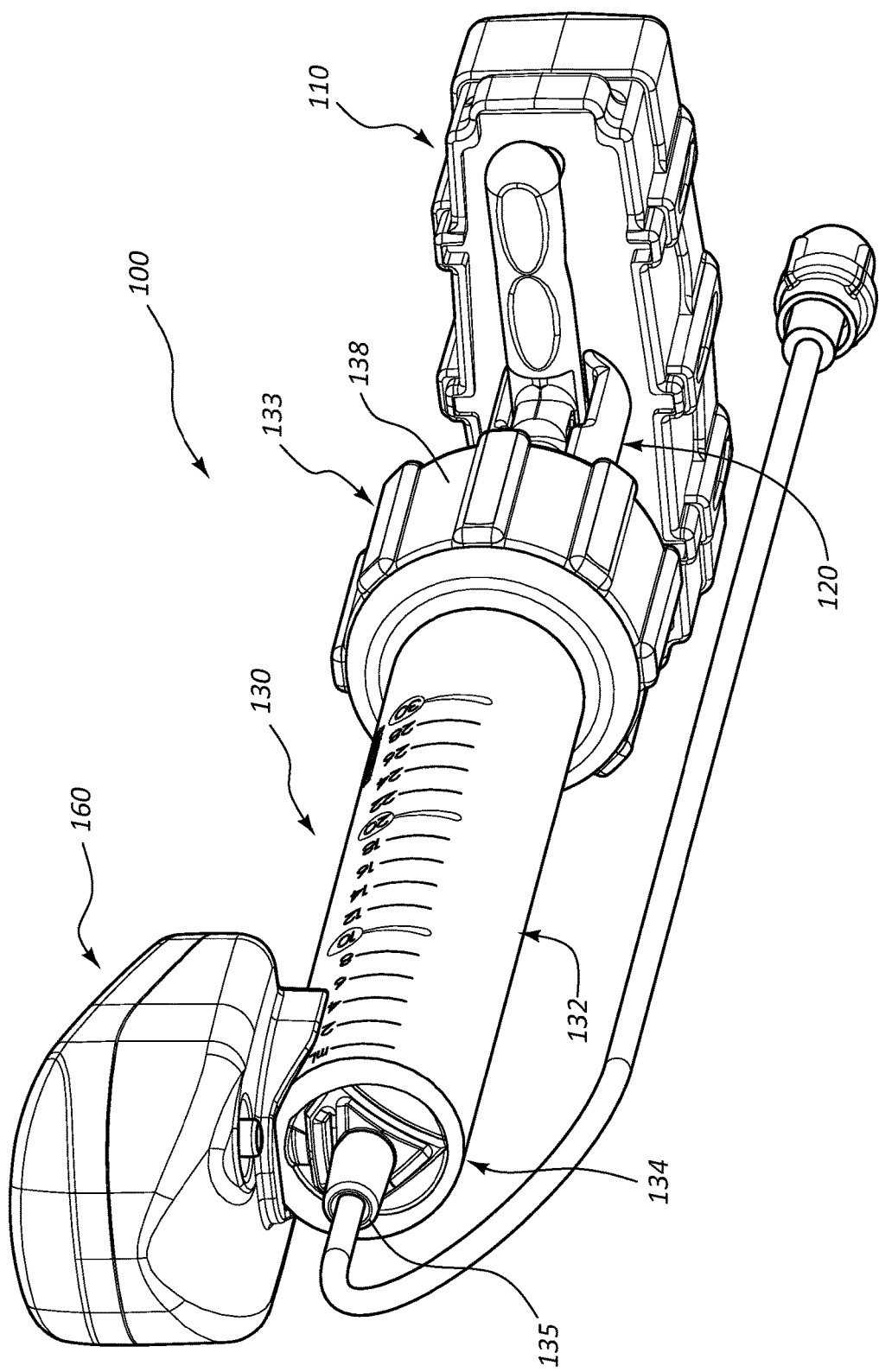
FIG. 1A is a perspective view of an inflation device.

An inflation device may comprise a syringe body. In some configurations, the syringe body may comprise a barrel, or syringe barrel, having a proximal end and a distal end, wherein the barrel is configured to receive a plunger. The syringe body may further comprise one or more stiffening ribs disposed on at least a portion of the barrel, for example, such as at the distal end of the barrel. Additionally, the syringe body may comprise a stiffening lip disposed around at least a portion of a circumference of the distal end of the barrel. The one or more stiffening ribs and/or the stiffening lip may be configured to reinforce and/or support at least a portion of the syringe body. In some instances, the syringe body may be configured to withstand pressures within a fluid reservoir of the syringe body of up to about 81 atmospheres (atm); and/or of up to about 109 atm; and/or in excess of 109 atm. In some embodiments, the syringe body may also be configured for use at pressures between about 0 atm and about 81 atm and/or of between about 0 atm and about 109 atm.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. Components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is the portion at the opposite end. For example, the proximal end of a syringe body is defined as the end closest to the practitioner during utilization of the syringe body (i.e., in connection with an inflation device). The distal end is the end opposite the proximal end, along the longitudinal direction of the syringe body.

The term "fluid" is used in its broadest sense, to refer to any fluid, including both liquids and gases as well as solutions, compounds, suspensions, etc., which generally behave as fluids.

Figure 1B:
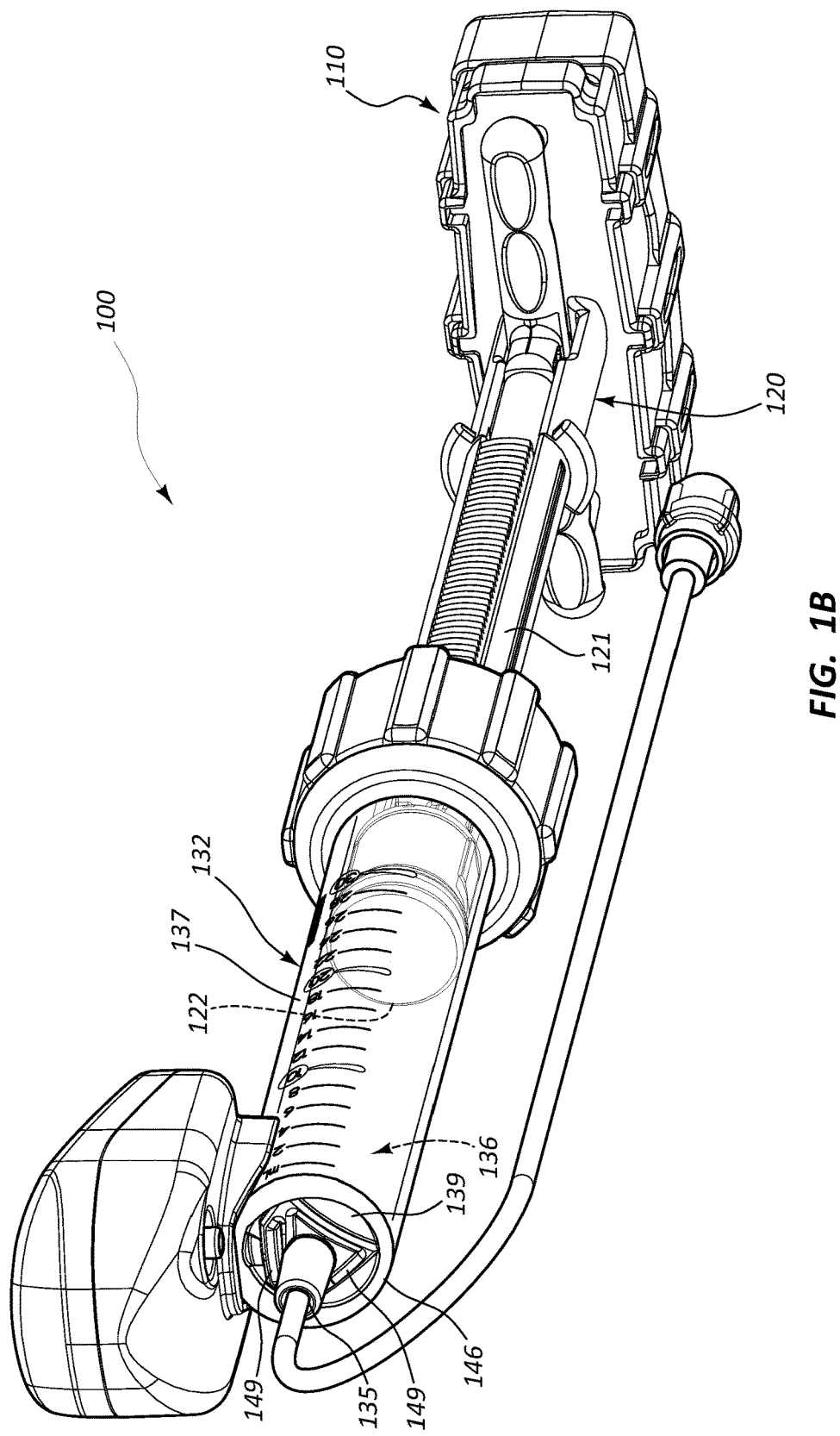
FIG. 1B is another perspective view of the inflation device of FIG. 1A.
Figure 1C:
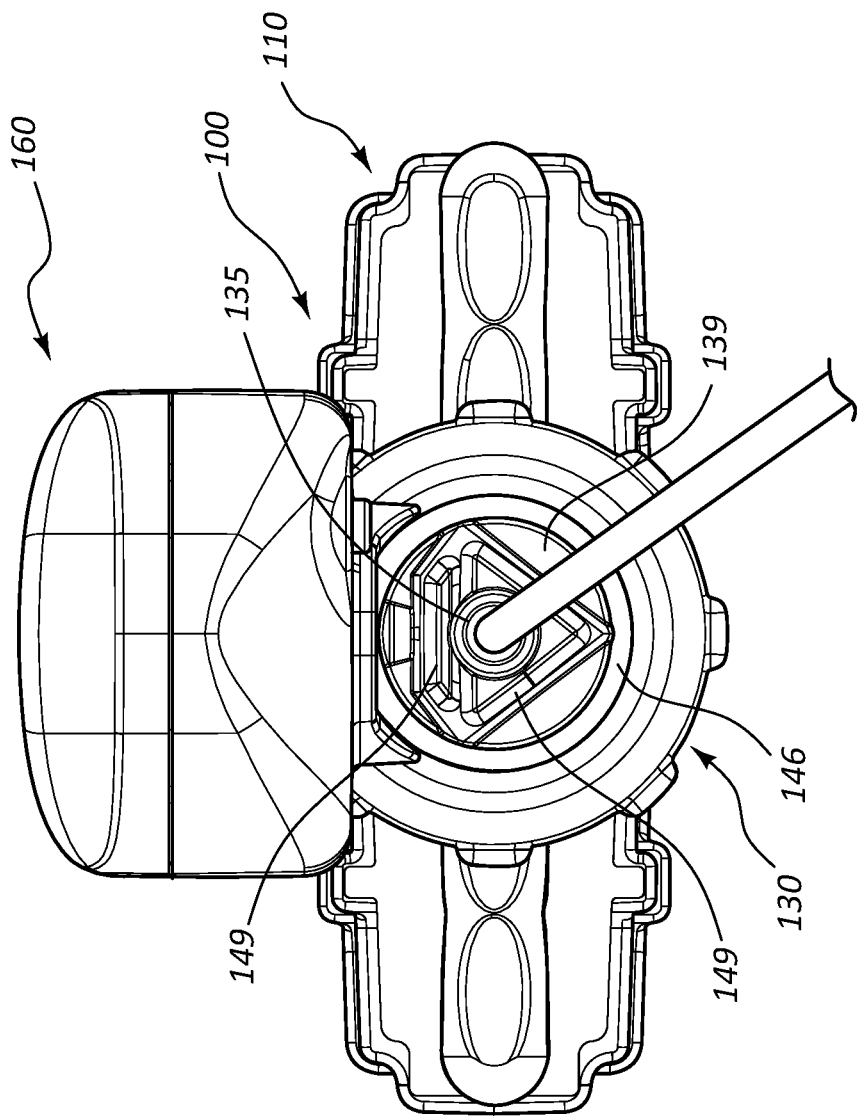
FIG. 1C is a distal end view of the inflation device of FIG. 1A.

FIGS. 1A-1C illustrate different views of an inflation device comprising a syringe body. FIGS. 2A-10 illustrate different views of the syringe body. In certain views, the syringe body may be coupled to, or shown with, additional components not included in every view. Further, in some views, only selected components are illustrated, to provide detail into the relationship of the components. Some components may be shown in multiple views, but not discussed in connection with every view. Disclosure provided in connection with a figure is relevant and applicable to disclosure provided in connection with any other figure.

Any and every component disclosed in connection with any of the exemplary syringe configurations herein may be optional. That is, though the syringe broadly refers to the components configured to receive the plunger, use of the term "syringe" is not meant to indicate that every disclosed syringe component is always present. Rather, the term is used broadly, referring to the collection of components, but not specifically referring to or requiring the inclusion of any particular component. Likewise, other broad groupings of components disclosed herein, such as the handle and the plunger, may also refer to collections of individual subcomponents. Use of these terms should also be considered non-limiting, as each subcomponent may or may not be present in every embodiment.

FIG. 1A is a perspective view of an inflation device 100. The inflation device 100 may include four broad groups of components; each group may have numerous subcomponents and parts. The four broad component groups are: a syringe 130, a plunger 120, a handle 110, and a display housing 160. In some embodiments, the inflation device 100 may be a device used to pressurize, depressurize, and/or otherwise displace and/or pressurize fluid along a line in order to inflate or deflate a medical device such as a balloon.

The syringe 130, as illustrated, can comprise a syringe body 132 formed of a generally cylindrical hollow tube configured to receive the plunger 120. The syringe body 132 may comprise an inlet/outlet port 135 disposed at or adjacent a distal end 134 of the syringe body 132. A coupling member 138 can also be coupled to the syringe body 132 at or adjacent a proximal end 133 of the syringe body 132. The coupling member 138 may include a center hole configured to allow the plunger 120 to pass through the coupling member 138 and into the syringe body 132. Further, the syringe body 132 may include threads 131 (see FIG. 2A) configured to selectively couple the syringe body 132 to the coupling member 138.

The handle 110 broadly refers to the group of components coupled to the proximal end of the plunger 120, some of which may be configured to be graspable by a user. In certain embodiments, the handle 110 may be configured such that the user may manipulate the position of the plunger 120 by manipulating the handle 110. Further, in some embodiments, the handle 110 may be an actuator mechanism configured to manipulate components of the inflation device 100.

FIG. 1B is another perspective view of the inflation device 100 of FIG. 1A, wherein at least a portion of the subcomponents and parts disposed within the syringe body 132 are visible. As illustrated, the plunger 120 can comprise a plunger shaft 121 coupled to a plunger seal 122 at a distal end of the plunger shaft 121. The plunger 120 may be configured to be longitudinally displaceable within the syringe body 132. The plunger shaft 121 may also be coupled to the handle 110 at a proximal end of the plunger shaft 121, with the plunger shaft 121 spanning the distance between the plunger seal 122 and the handle 110.

The syringe body 132 may be configured for use in connection with the inflation device 100 (e.g., a high-pressure inflation device). As shown in FIG. 1B, the syringe body 132 can comprise a first wall 137, wherein the first wall 137 at least partially defines a fluid reservoir or void 136. The fluid reservoir 136 may be configured to receive at least a portion of the plunger 120. The syringe body 132 may further comprise a second wall 139, wherein the second wall 139 can be disposed at a distal end of the fluid reservoir 136. The shape of the second wall 139 can be substantially circular. As illustrated, the fluid reservoir 136 may be defined by a space or void at least partially enclosed by the first wall 137 and disposed between each of the plunger seal 122 and the second wall 139. Accordingly, displacement of the plunger seal 122 with respect to the syringe body 132 can alter the size and volume of the fluid reservoir 136.

As shown, the second wall 139 may comprise at least one stiffening rib 149, which is described in more detail below. The syringe body 132 can also comprise the inlet/outlet port 135, wherein the inlet/outlet port 135 may be disposed in at least a portion of the second wall 139. The inlet/outlet port 135 may be configured to allow or permit a fluid to flow into or out of the fluid reservoir 136 (i.e., upon displacement of the plunger 120). Furthermore, a distal end of the first wall 137 may extend distally relative to the second wall 139 along at least a portion of a circumference of the second wall 139 forming a substantially annular stiffening lip 146, which is also described in more detail below.

FIG. 1C is a distal end view of the inflation device 100 of FIG. 1A, illustrating a relationship of the handle 110, the syringe 130, the display housing 160, and a subset of the subcomponents thereof, according to an embodiment of the present disclosure. For example, the stiffening lip 146, as illustrated, is disposed around the circumference of the second wall 139, and a plurality of stiffening ribs 149 is disposed on the exterior surface of the second wall 139. Additionally, the inlet/outlet port 135 is disposed in a center portion of the second wall 139. In some embodiments, the inlet/outlet port 135 may be disposed in another portion of the second wall 139 or in another portion of the syringe 130. For example, the inlet/outlet port 135 may be disposed at or adjacent an edge portion of the second wall 139.

Figure 2A:
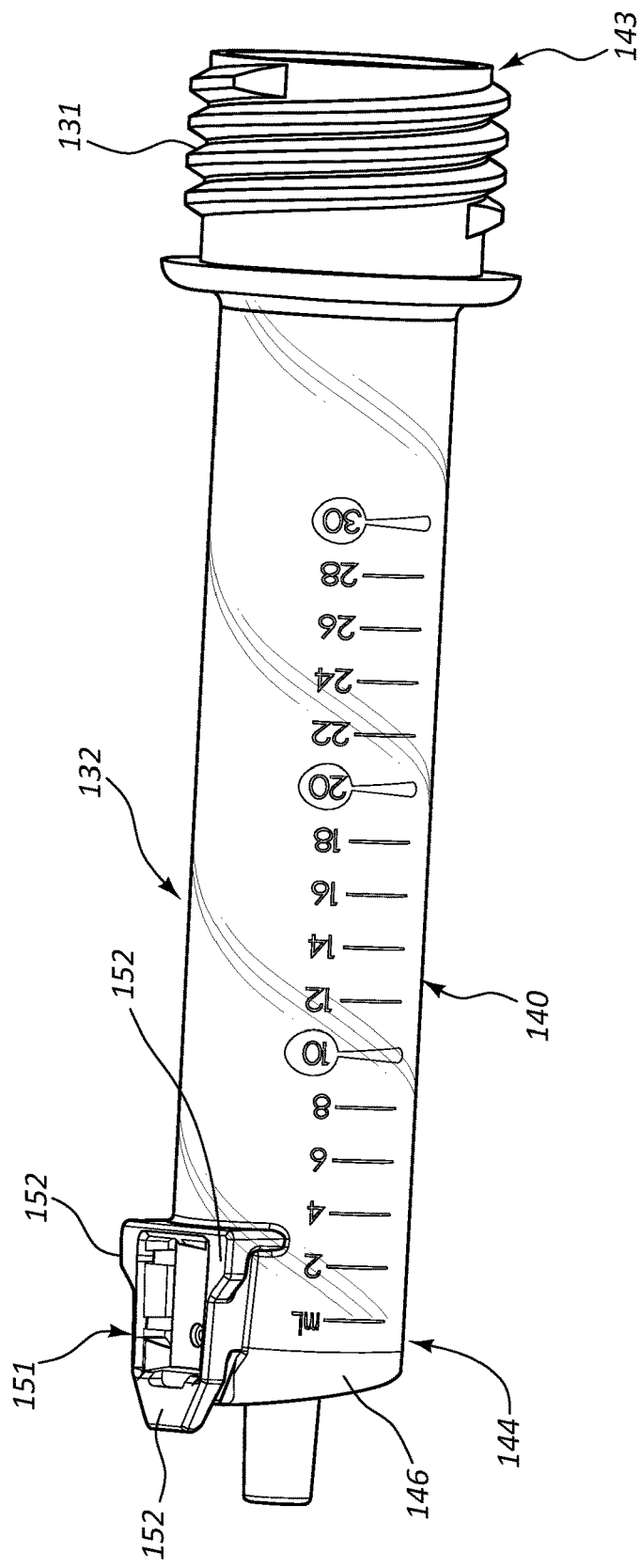
FIG. 2A is a side view of a syringe body.

FIG. 2A is a side view of the syringe body 132 of FIG. 1A. As illustrated, the syringe body 132 may comprise a barrel or syringe barrel 140. The barrel 140 may comprise a proximal end 143 and a distal end 144. In some embodiments, the barrel 140 may be configured to receive the plunger 120 (see FIGS. 1A and 1B). The syringe body 132 may further comprise the stiffening lip 146 disposed around at least a portion of the circumference of the distal end 144 of the barrel 140. In certain embodiments, the stiffening lip 146 may be disposed around the entire circumference, or substantially the entire circumference, of the distal end 144 of the barrel 140. In certain other embodiments, the stiffening lip 146 may be disposed around only a portion of the circumference of the distal end 144 of the barrel 140. For example, the stiffening lip 146 may be disposed around about 10% to about 100% of the circumference of the distal end 144 of the barrel 140, the stiffening lip 146 may be disposed around about 25% to about 100% of the circumference of the distal end 144 of the barrel 140, the stiffening lip 146 may be disposed around about 50% to about 100% of the circumference of the distal end 144 of the barrel 140, or the stiffening lip 146 may be disposed around about 75% to about 100% of the circumference of the distal end 144 of the barrel 140.

In some embodiments, the stiffening lip 146 may be discontinuous. For example, the stiffening lip 146 may comprise two or more segments, wherein a first segment is disposed around a first portion of the circumference of the distal end 144 of the barrel 140, wherein a second segment is disposed around a second portion of the circumference of the distal end 144 of the barrel 140, and wherein the first segment of the stiffening lip 146 and the second segment of the stiffening lip 146 are discontinuous. In certain embodiments, the stiffening lip 146 may comprise three discontinuous segments, four discontinuous segments, five discontinuous segments, and so on.

With reference again to FIG. 2A, the syringe body 132 may further comprise one or more features configured for coupling a secondary component to the syringe body 132, such as an adaptor 151. In some other embodiments, the syringe body 132 may not comprise an adaptor. The adaptor 151 may be coupled to the syringe body 132. In some embodiments, the adaptor 151 may be integrally formed with the syringe body 132. As illustrated, the adaptor 151 can comprise one or more secondary component mounting features 152. The adaptor 151 and/or the one or more secondary component mounting features 152 may be configured for coupling the syringe body 132 to the display housing 160 (see FIGS. 1A-1C) or any other suitable secondary component. In various embodiments, the adaptor 151 and/or the one or more secondary component mounting features 152 may be configured for mounting the display housing 160, or any other suitable secondary component, on the syringe body 132.

In some configurations, there may be a greater stress load on at least a portion of the syringe body 132 at or adjacent the adaptor 151. For example, at least a portion of the syringe body 132 at or adjacent the adaptor 151 may be exposed to, or under, more stress (i.e., mechanical stress) than other portions of the syringe body 132. One or more stiffening ribs and/or at least a portion of the stiffening lip 146 disposed at or adjacent the adaptor 151 may reinforce or support at least a portion of the syringe body 132 and/or the barrel 140.

Figure 2B:
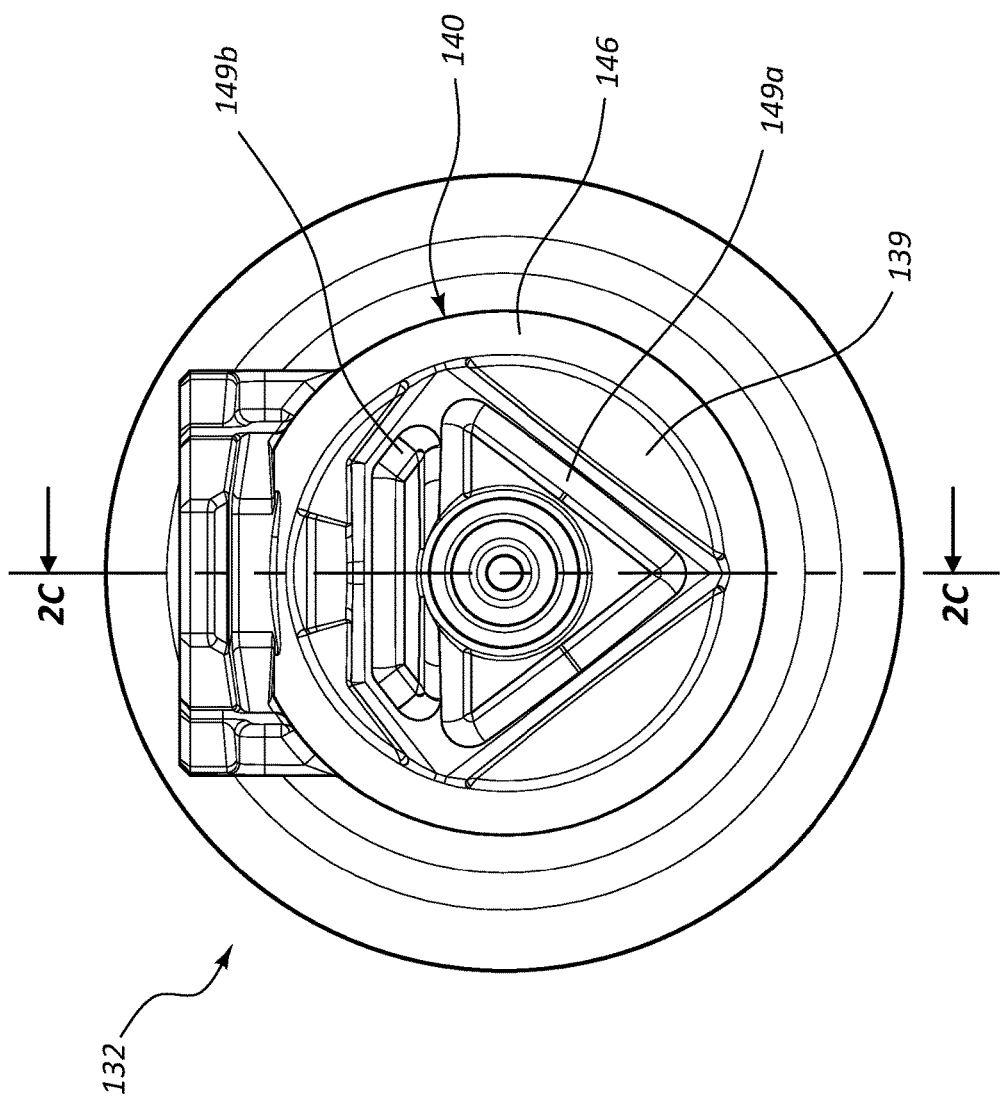
FIG. 2B is a distal end view of the syringe body of FIG. 2A.

FIG. 2B is a distal end view of the syringe body 132 of FIG. 2A. As illustrated, the syringe body 132 may comprise a first stiffening rib 149*a* and a second stiffening rib 149*b* disposed on at least a portion of the distal end of the barrel 140 (i.e., on the second wall 139). The stiffening lip 146 may also be disposed at the distal end of the barrel 140 (i.e., around at least a portion of the circumference of the second wall 139). In certain embodiments, each of the stiffening ribs and the stiffening lip may be an integrally formed feature extending from the syringe body. For example, a stiffening rib and a stiffening lip may be a single, unitary feature. In certain other embodiments, each of the stiffening ribs and the stiffening lip may be separately formed elements coupled to the syringe body.

With reference back to FIGS. 1A and 1B, as the plunger 120 is displaced within the syringe body 132, pressure may be generated within the fluid reservoir 136. For example, up to about 50 atm of pressure may be generated within the fluid reservoir 136, up to about 60 atm of pressure may be generated within the fluid reservoir 136, up to about 70 atm of pressure may be generated within the fluid reservoir 136, up to about 81 atm of pressure may be generated within the fluid reservoir 136, or up to about 109 atm of pressure may be generated within the fluid reservoir 136. In some embodiments, about 0 atm to about 81 atm of pressure may be generated within the fluid reservoir 136. In certain embodiments, about 0 atm to about 109 atm of pressure may be generated within the fluid reservoir 136.

The syringe body 132 and/or the barrel 140 may be configured to withstand pressures within the fluid reservoir 136 of at least about 50 atm, about 60 atm, about 70 atm, about 81 atm, and about 109 atm. The stiffening lip 146 and/or the stiffening ribs 149 (e.g., the first stiffening rib 149*a* and the second stiffening rib 149*b*), as described herein, may reinforce or support at least a portion of the syringe body 132 and/or the barrel 140, such that the syringe body 132 and/or the barrel 140 may avoid or resist breaking, bursting, cracking, deforming, or otherwise failing under certain conditions (i.e., under certain pressures within the fluid reservoir 136). For example, a first portion of the syringe body 132 and/or the barrel 140 (i.e., a portion of the distal end of the barrel 140) may be subjected to a higher stress load than a second portion of the syringe body 132 and/or the barrel 140 when pressure increases within the fluid reservoir 136. For example, there may be stress, or increased stress, at a joint and/or a juncture of two or more components of the syringe body 132 and/or the barrel 140. Accordingly, the first portion of the syringe body 132 and/or the barrel 140 may be more liable or prone to break, burst, crack, deform, or otherwise fail before the second portion of the syringe body 132. Disposition of one or more stiffening lips 146 and/or one or more stiffening ribs 149 at or adjacent such a portion of the syringe body 132 and/or the barrel 140 (i.e., the first portion) may limit or prevent failure of the syringe body 132 and/or the barrel 140.

Failure of a syringe body may limit the maximum pressure at which an inflation device may be used. For example, when the syringe body fails (i.e., breaks, bursts, cracks, and/or deforms) a rapid pressure drop within the syringe body may result. When a medical device is coupled to the inflation device, this may also result in a rapid, unexpected pressure drop in the medical device.

The shape of the stiffening ribs 149 may vary. As shown in FIG. 2B, for example, the shape of the first stiffening rib 149*a* can be substantially triangular and the shape of the second stiffening rib 149*b* can be substantially trapezoidal. In various embodiments, the shape of a first plurality of stiffening ribs may be substantially triangular and the shape of a second plurality of stiffening ribs may be substantially trapezoidal. In other embodiments, the shape of the stiffening ribs 149 can be substantially circular, substantially linear, substantially oval, substantially rectangular, or substantially square. Any other suitable shape can also be used. For example, the shape of the stiffening ribs 149 can be irregular (i.e., not a traditionally defined shape). Likewise, the shape of the stiffening lip 146 can also vary. As shown in FIG. 2B, for example, the stiffening lip 146 can be substantially circular. The shape of the stiffening lip 146 may vary, at least in part, due to a variety of factors such as the shape of the syringe body 132 and/or the barrel 140.

In some embodiments, the syringe body may comprise two or more stiffening ribs. In such embodiments, each stiffening rib may have a different shape, each stiffening rib may have substantially the same shape, or the stiffening ribs may have any combination of shapes (i.e., a first and a second stiffening rib may be substantially circular while a third stiffening rib may be substantially linear).

The one or more stiffening ribs may form a substantially diamond shape. As shown in FIG. 2B, for example, the first stiffening rib 149*a* can be substantially triangular and the second stiffening rib 149*b* can be substantially trapezoidal. Further, the substantially triangular first stiffening rib 149*a* can be disposed adjacent the substantially trapezoidal second stiffening rib 149*b* such that a substantially diamond shape is formed. In various other embodiments, a single stiffening rib or three or more stiffening ribs may also form a substantially diamond shape.

In some embodiments, a first stiffening rib may define a first chord along an exterior surface of the second wall, a second stiffening rib may define a second chord along an exterior surface of the second wall, and/or a third stiffening rib may define a third chord along the exterior surface of the second wall, etc. Other configurations of the one or more stiffening ribs are also within the scope of this disclosure. For example, one or more stiffening ribs may form a hub and spoke shape (i.e., each of the one or more stiffening ribs may radiate outward from a center portion of the second wall). In another example, the one or more stiffening ribs may form a star shape. In certain embodiments, the configuration of the one or more stiffening ribs and/or the stiffening lip may at least partially determine the maximum pressure at which a fluid reservoir may be pressurized prior to failure of a syringe body.

Figure 2C:
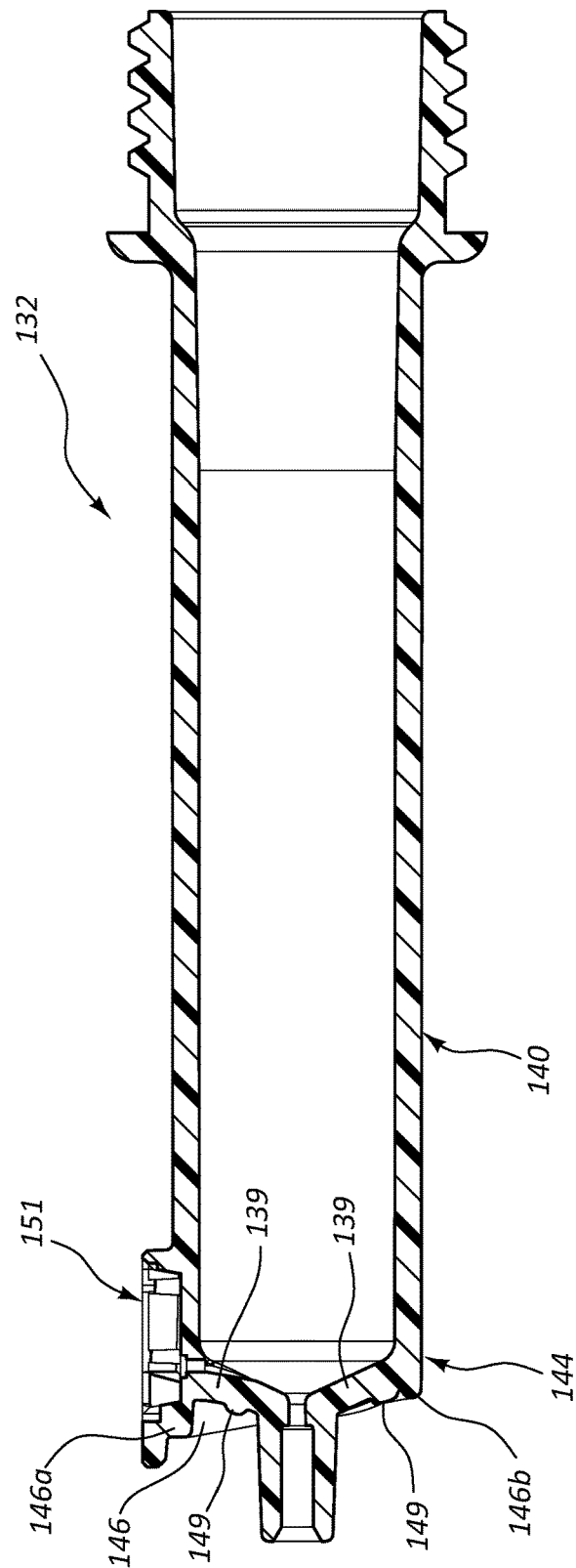
FIG. 2C is a cross sectional view of the syringe body of FIG. 2B taken through line 2C-2C.

FIG. 2C is a cross sectional view of the syringe body 132 of FIG. 2B taken through line 2C-2C. In the illustrated embodiment, the stiffening lip 146 can extend distally in relation to an exterior surface of the distal end 144 of the barrel 140. Likewise, the one or more stiffening ribs 149 may extend distally in relation to the exterior surface of the distal end 144 of the barrel 140. Stated another way, each of the stiffening lip 146 and/or the one or more stiffening ribs 149 may extend distally in relation to an exterior surface of the second wall 139.

In some embodiments, a first stiffening rib may extend more distally than a second stiffening rib. For example, the syringe body 132 may comprise a plurality of stiffening ribs 149, wherein each of the plurality of stiffening ribs 149 may extend a different distance. Alternatively, each of the plurality of stiffening ribs 149 may extend substantially the same distance. Other combinations of stiffening rib 149 extension distances or height (i.e., the distance of the extension of the stiffening rib 149 from the exterior surface of the distal end 144 of the barrel 140) are also within the scope of this disclosure.

In some other embodiments, the one or more stiffening ribs may extend proximally in relation to an interior surface of the distal end of the barrel (not shown). For example, the one or more stiffening ribs may be disposed within the fluid reservoir.

Referring again to FIG. 2C, the stiffening lip 146 may comprise a first portion 146a and a second portion 146b, wherein the first portion 146a is disposed opposite, or substantially opposite, of the second portion 146b. Each of the first portion 146a and the second portion 146b may extend distally in relation to the exterior surface of the distal end 144 of the barrel 140. As shown, a height of the first portion 146a may be greater than a height of the second portion 146b. In some other embodiments, the height of the first portion 146a may be less than the height of the second portion 146b. In yet some other embodiments, the height of the first portion 146a may be substantially the same as the height of the second portion 146b. The stiffening lip 146 may also comprise one portion, three portions, four portions, five portions, or any other suitable number of portions, wherein each portion has a height that may vary in relation to the height of any other portion.

The first portion 146a of the stiffening lip 146, as illustrated, can be disposed adjacent the adaptor 151. As discussed above, there may be a greater stress load on at least a portion of the syringe body 132 at or adjacent the adaptor 151. For example, the adaptor 151 may be coupled to a display housing or another suitable secondary component. As such, a portion of a stiffening lip 146 having an increased or greater height relative to another portion of the stiffening lip 146, disposed at or adjacent the adaptor 151, may reinforce or support at least a portion of the syringe body 132 and/or the barrel 140. For example, the first portion 146a, as illustrated, may reinforce or support a portion of the syringe body 132 at or adjacent the adaptor 151.

Figure 3:
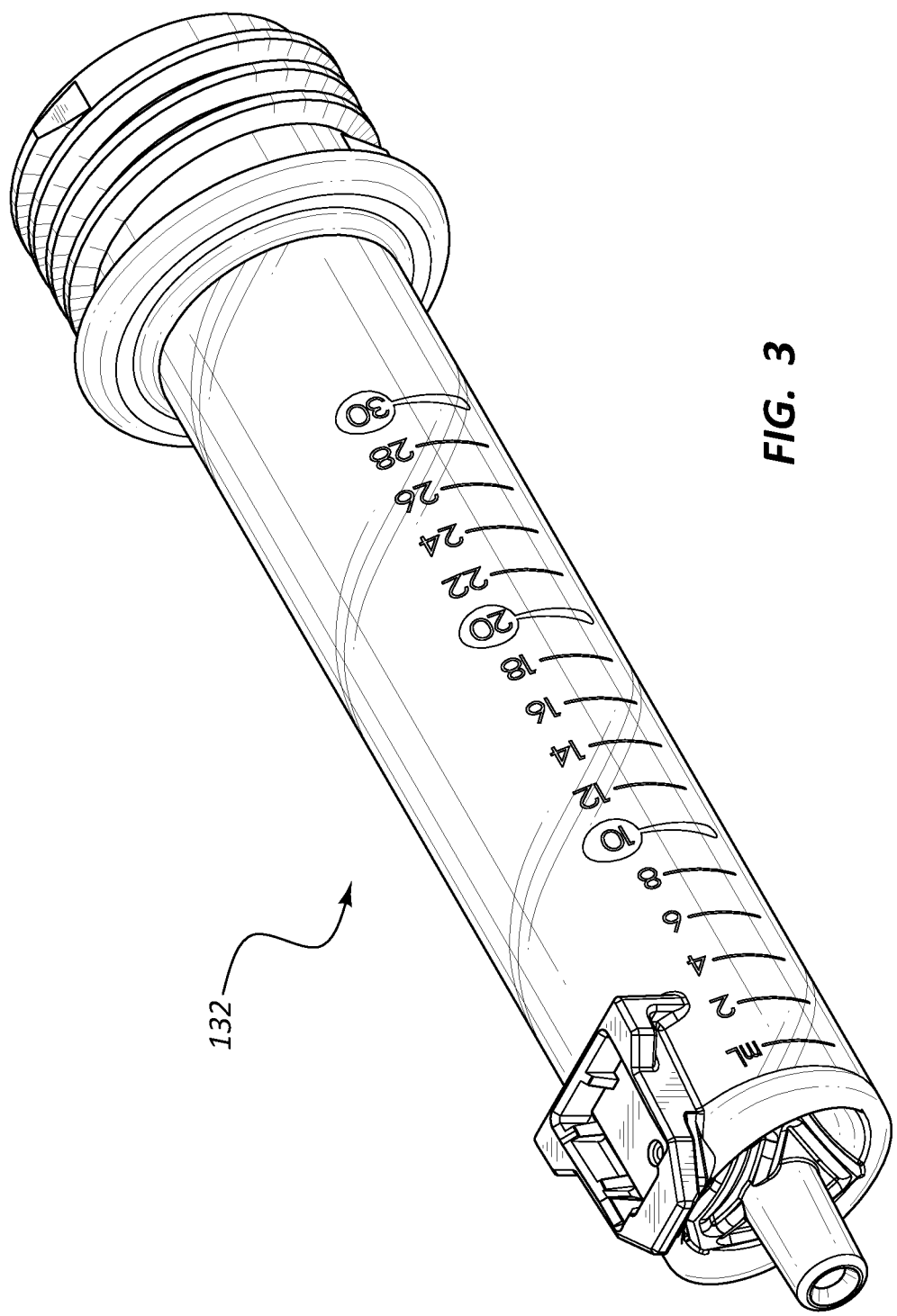
FIG. 3 is a perspective view of the syringe body of FIG. 2A.
Figure 4:
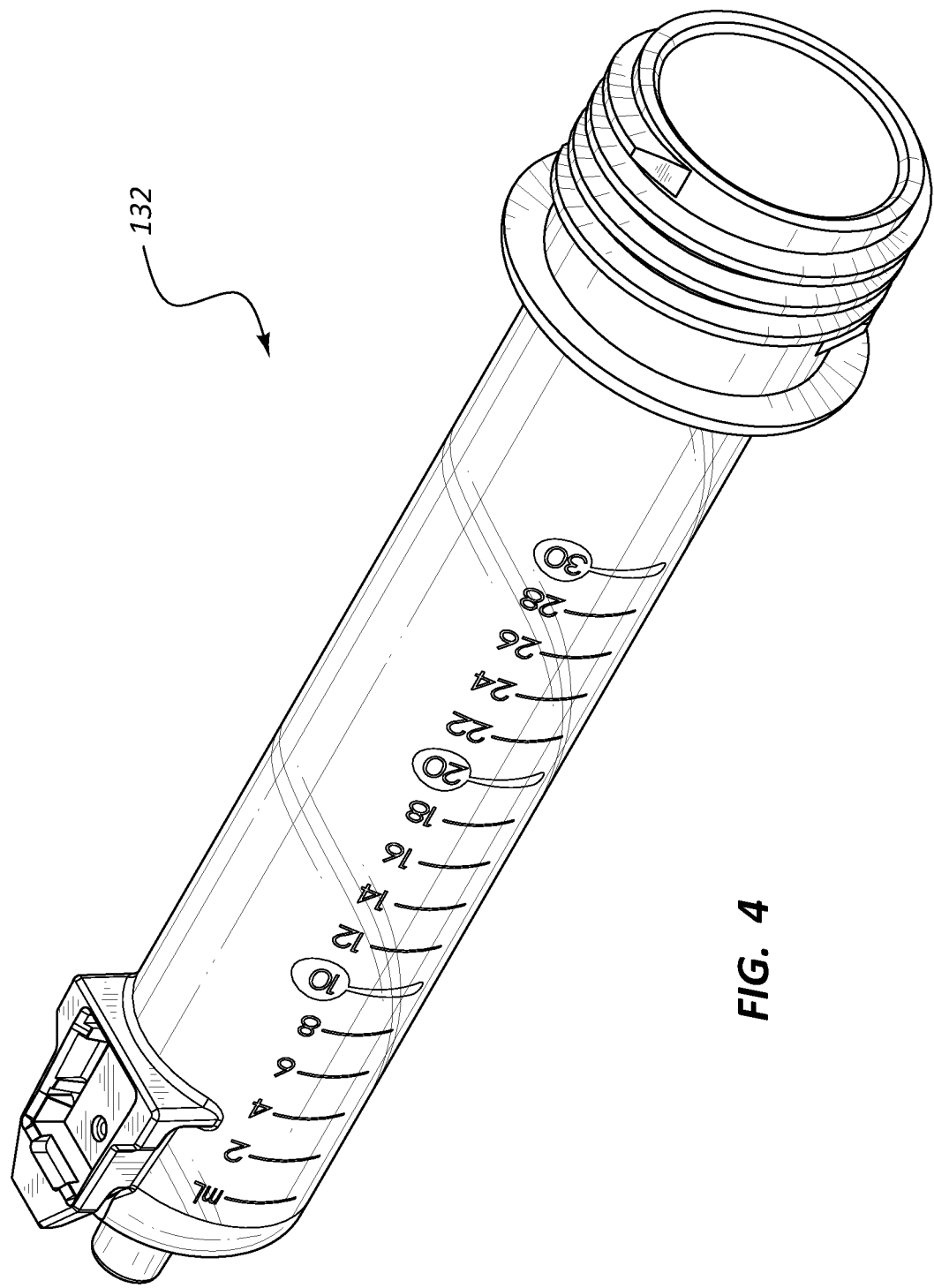
FIG. 4 is a second perspective view of the syringe body of FIG. 2A.
Figure 5:
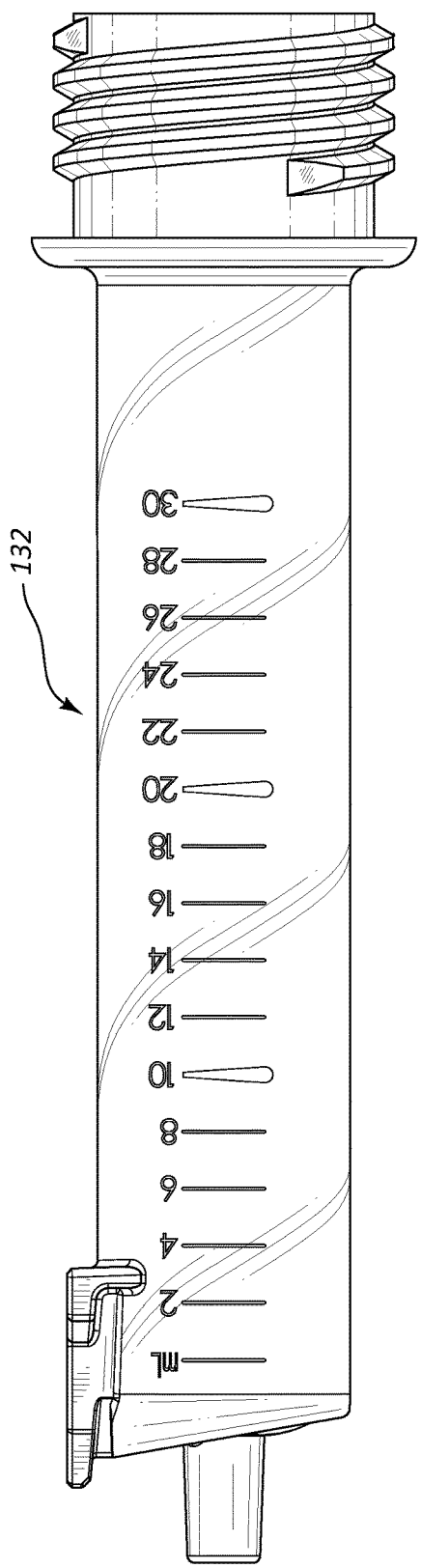
FIG. 5 is a front view of the syringe body of FIG. 2A.
Figure 6:
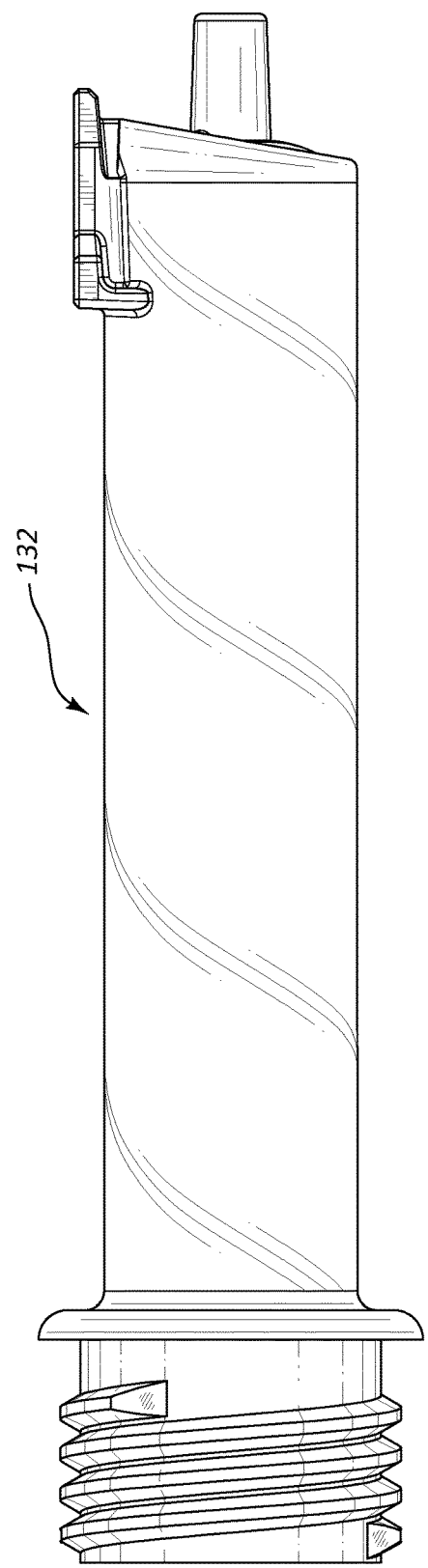
FIG. 6 is a back view of the syringe body of FIG. 2A.
Figure 7:
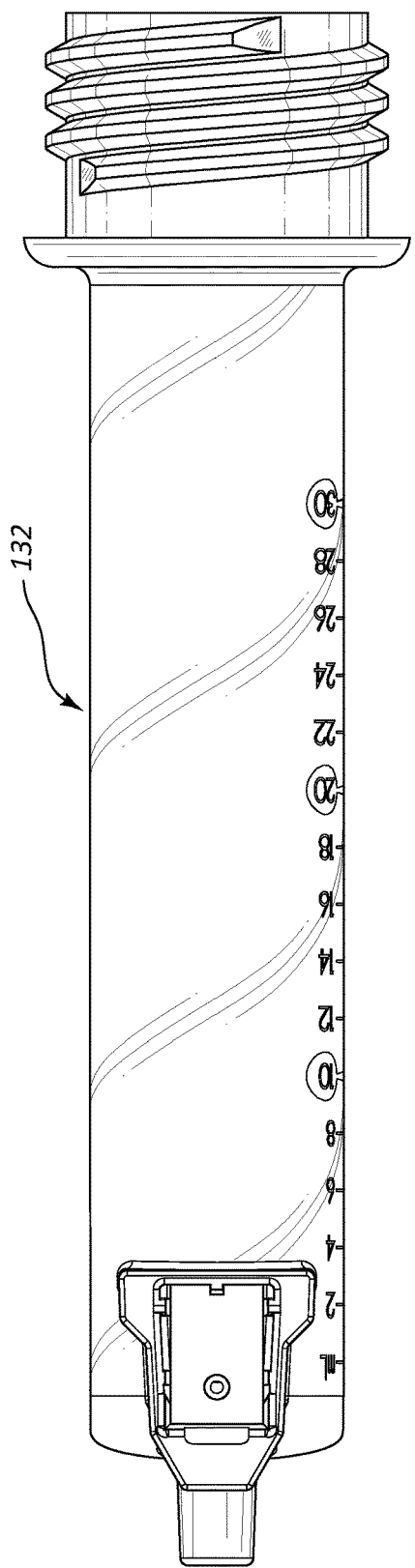
FIG. 7 is a left side view of the syringe body of FIG. 2A.
Figure 8:
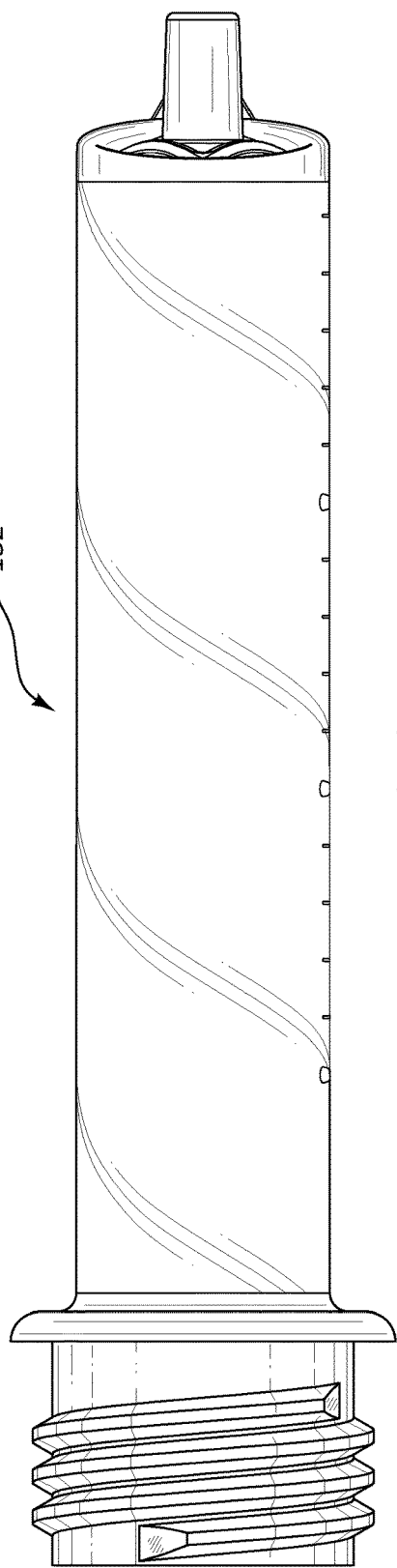
FIG. 8 is a right side view of the syringe body of FIG. 2A.
Figure 10:
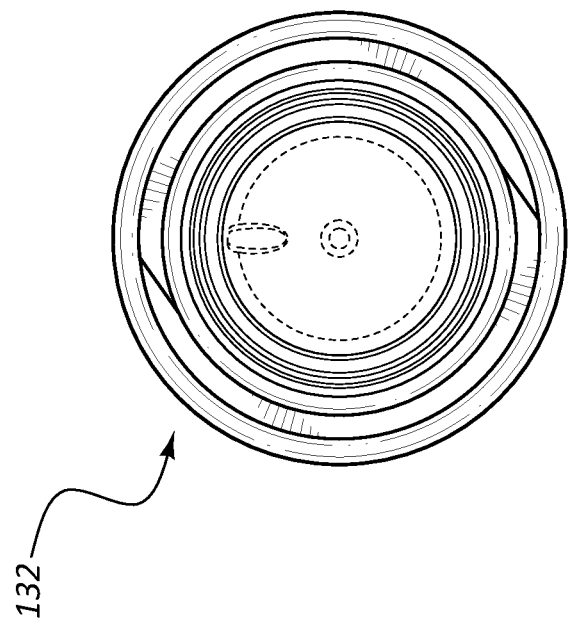
FIG. 10 is a top view of the syringe body of FIG. 2A.
Figure 9:
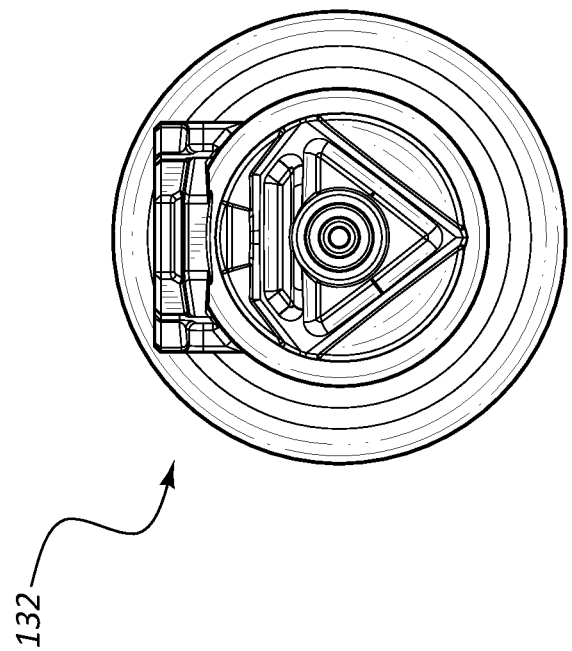
FIG. 9 is a bottom view of the syringe body of FIG. 2A.

FIG. 3 is a perspective view of the syringe body 132 of FIG. 2A. FIG. 4 is a second perspective view of the syringe body 132 of FIG. 2A. FIG. 5 is a front view of the syringe body 132 of FIG. 2A. FIG. 6 is a back view of the syringe body 132 of FIG. 2A. FIG. 7 is a left side view of the syringe body 132 of FIG. 2A. FIG. 8 is a right side view of the syringe body 132 of FIG. 2A. FIG. 9 is a bottom view of the syringe body 132 of FIG. 2A. FIG. 10 is a top view of the syringe body 132 of FIG. 2A.

Figure 11:
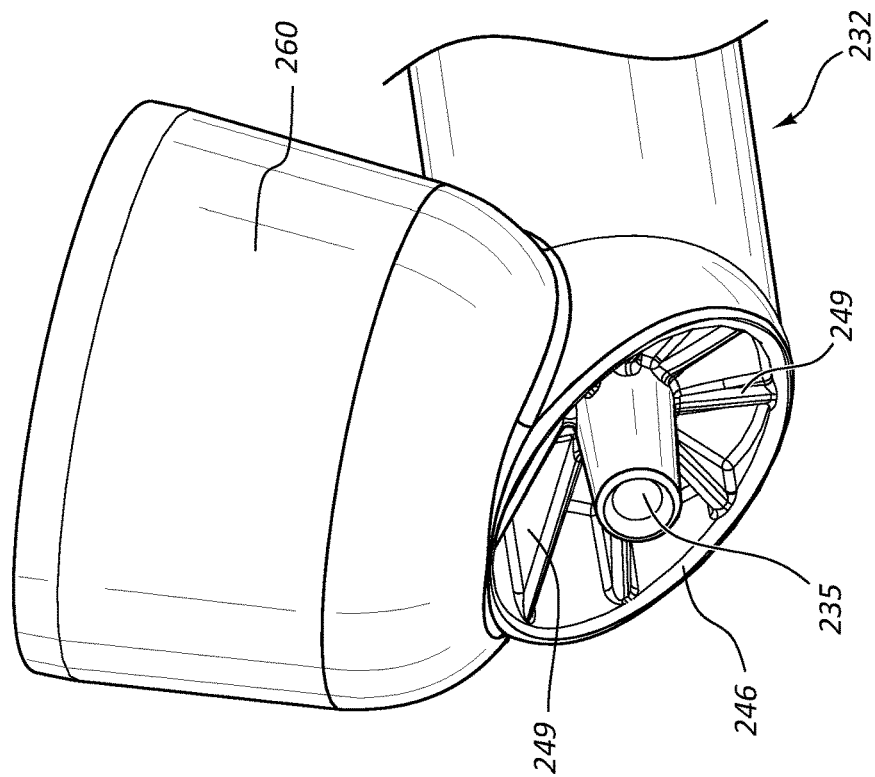
FIG. 11 is perspective view of a portion of another embodiment of a syringe body.

FIG. 11 is a perspective view of a portion of a syringe body 232 that resembles the syringe body 132 described above in certain respects. Accordingly, like features are designated with like reference numerals, with the leading digits incremented to "2." For example, the embodiment depicted in FIG. 11 includes a stiffening lip 246 that may, in some respects, resemble the stiffening lip 146 of FIGS. 1-10. Relevant disclosure set forth above regarding similarly identified features thus may not be repeated hereafter. Moreover, specific features of the syringe body and related components shown in FIGS. 1-10 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the syringe body 232 and related components depicted in FIG. 11. Any suitable combination of the features, and variations of the same, described with respect to the syringe body 132 and related components illustrated in FIGS. 1-10 can be employed with the syringe body 232 and related components of FIG. 11, and vice versa. This pattern of disclosure applies equally to further embodiments depicted in subsequent figures and described hereafter, wherein the leading digits may be further incremented.

Figure 12:
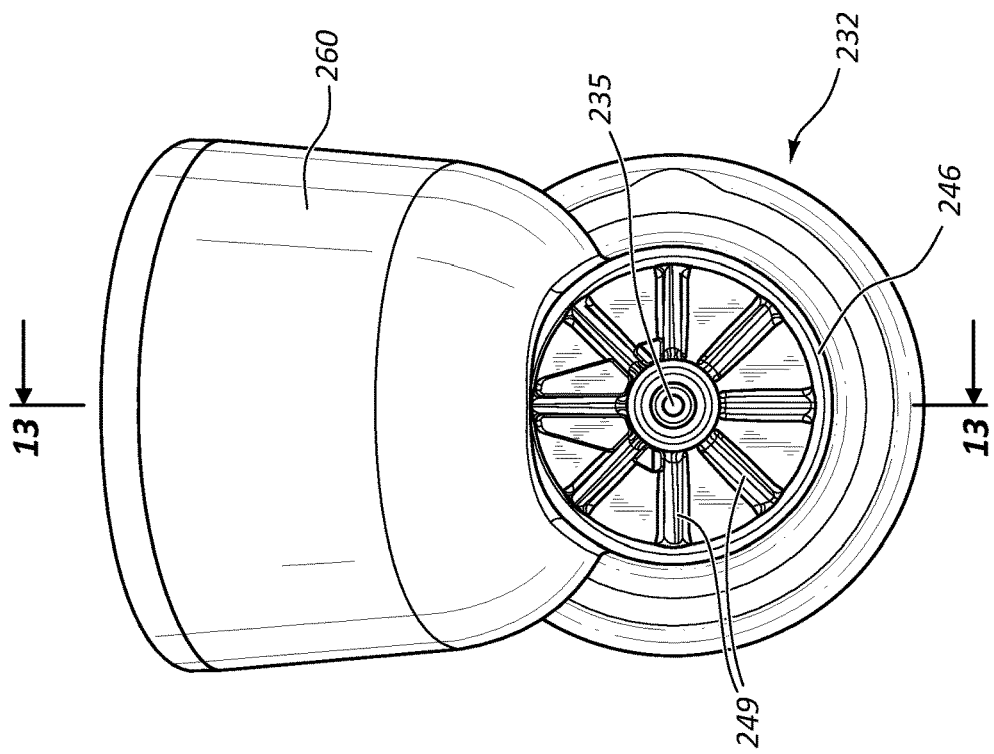
FIG. 12 is a front view of the portion of the syringe body of FIG. 11.
Figure 13:
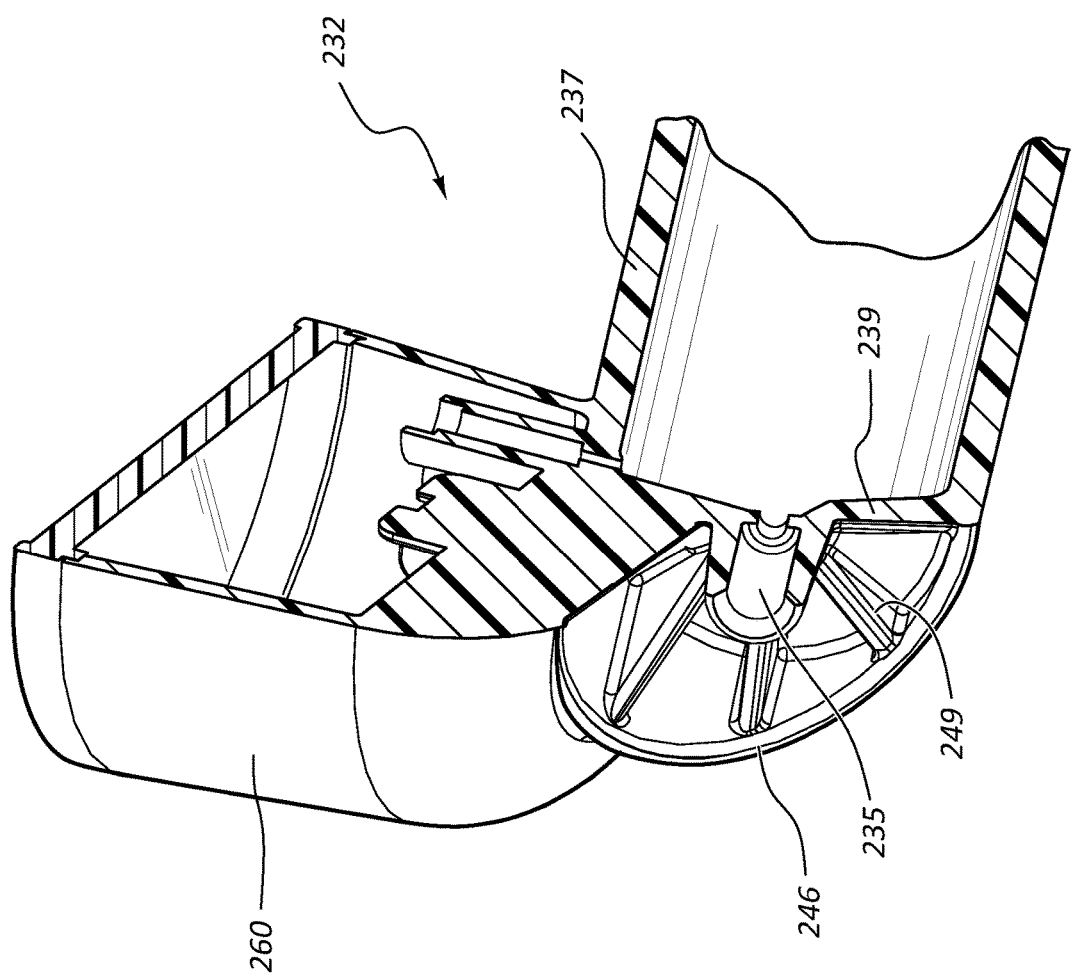
FIG. 13 is cross sectional perspective view of the portion of the syringe body of FIG. 11.

As shown in FIGS. 11, 12, and 13, the syringe body 232 may comprise a first wall 237 and a second wall 239 defining a fluid reservoir. An inlet/outlet port 235 may be in fluid communication with the fluid reservoir. In the illustrated embodiment, the syringe body further comprises a display housing 260. In some embodiments, the display housing 260 may be integrally formed with the syringe body 232.

The syringe body 232 may comprise a stiffening lip 246 and one or more stiffening ribs 249. The stiffening lip 246 and stiffening ribs 249 may be disposed at or adjacent the distal end of the syringe body 232. As with the stiffening ribs 149 and stiffening lip 146 may provide structural support, reinforcement, strength, stiffness, and/or other properties or attributes to the syringe body 232.

In the embodiment of FIGS. 11, 12, and 13, the stiffening lip 246 extends around a circumference of the syring body 232 and may define an annular ring. The stiffening ribs 249 may extend radially in from the stiffening lip 246 toward the center of the syringe body 232. For example, the stiffening ribs 249 may extend inward along a radius of the syringe body 232. In other embodiments the stiffening ribs 249 may be disposed along a chord of the syringe body 232.

Further, in some embodiments, for example embodiments wherein the stiffening ribs 249 extend toward the center of the syringe body 232, the stiffening ribs 249 may extend distally to the same longitudinal position of the stiffening lip 246, but may slope toward the center of the syringe body 232. In other words, the stiffening ribs 249 may extend to a different height, and/or be taller, adjacent the circumference of the syringe body 232 and shorter toward the center of the syringe body 232. In some such embodiments, the stiffening ribs 249 may extend along a linear or continuous slope toward the center of the syringe body 232 and in other embodiments the stiffening ribs 249 may extend along a non-linear or discontinuous slope. In some instances, stiffening ribs 249 that are shorter toward the center of the syringe body 232 may accommodate or otherwise facilitate coupling of a tube or other element to the inlet/outlet port 235.

Methods related to use of syringe bodies, or syringe bodies configured for use in connection with inflation devices, are also disclosed herein. In some embodiments, a method of displacing a plunger of an inflation device (e.g., a high-pressure inflation device) may comprise obtaining an inflation device. The inflation device may comprise a syringe body and a plunger disposed within the syringe body. Further, the syringe body may comprise one or more stiffening ribs and/or a stiffening lip, wherein each of the one or more stiffening ribs and/or the stiffening lip are disposed at or adjacent a distal end of the syringe body. The syringe body may also comprise a fluid reservoir defined by a space at least partially enclosed by an inside surface of the syringe body and disposed between a plunger seal and the distal end of the syringe body. The method of displacing the plunger of the inflation device may further comprise displacing the plunger such that from about 0 atm to about 81 atm of pressure is generated within the fluid reservoir. The method of displacing the plunger of the inflation device may also further comprise displacing the plunger such that from about 0 atm to about 109 atm of pressure is generated within the fluid reservoir. In certain embodiments, the syringe body may be configured to withstand at least about 0 atm to about 81 atm of pressure within the fluid reservoir. In various embodiments, the syringe body may be configured to withstand at least about 0 atm to about 109 atm of pressure within the fluid reservoir. As can be appreciated, additional methods and/or method steps can be derived from FIGS. 1A-10 and the corresponding disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially circular" is recited with respect to a feature, it is understood that in further embodiments, the feature can have a precisely circular configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A syringe body configured for use in connection with a high-pressure inflation device, the syringe body comprising:
   a first wall defining a fluid reservoir, the fluid reservoir configured to receive a plunger;
   a second wall defining a distal end of the fluid reservoir, the second wall comprising:
      at least one stiffening rib; and
   an inlet/outlet port disposed in the second wall,
   wherein a distal end of the first wall extends distally relative to the second wall along a circumference of the second wall forming an annular stiffening lip,
   wherein the second wall defines an interior surface of the fluid reservoir extending between the first wall and the inlet/outlet port, and
   wherein the at least one stiffening rib extends inward of the annular stiffening lip along an exterior surface of the second wall.

2. The syringe body of claim 1, wherein the fluid reservoir is further defined by a space at least partially enclosed by the first wall and disposed between a plunger seal and the second wall.

3. The syringe body of claim 1, wherein the second wall is substantially circular.

4. The syringe body of claim 1, wherein a height of a first portion of the annular stiffening lip is greater than a height of a second portion of the annular stiffening lip.

5. The syringe body of claim 1, wherein the second wall comprises a plurality of stiffening ribs and wherein a shape of a first plurality of stiffening ribs is substantially triangular when viewed from a distal end of the syringe body.

6. The syringe body of claim 5, wherein a shape of a second plurality of stiffening ribs is substantially trapezoidal when viewed from the distal end of the syringe body.

7. The syringe body of claim 1, wherein the second wall comprises a plurality of stiffening ribs and wherein the plurality of stiffening ribs forms a substantially diamond shape when viewed from a distal end of the syringe body.

8. The syringe body of claim 1, wherein a first stiffening rib defines a first chord along the exterior surface of the second wall.

9. The syringe body of claim 8, wherein a second stiffening rib defines a second chord along the exterior surface of the second wall.

10. The syringe body of claim 9, wherein a third stiffening rib defines a third chord along the exterior surface of the second wall.

11. The syringe body of claim 1, wherein the syringe body is configured to withstand a pressure of up to at least about 81 atmospheres (atm) within the fluid reservoir.

12. The syringe body of claim 11, wherein the syringe body is configured to withstand a pressure of up to at least about 109 atm within the fluid reservoir.

13. The syringe body of claim 1, wherein a height of a first portion of the at least one stiffening rib is greater than a height of a second portion of the at least one stiffening rib.

14. The syringe body of claim 13, wherein the second portion of the at least one stiffening rib is disposed radially inward, with respect to the syringe body, of the first portion of the at least one stiffening rib.

15. The syringe body of claim 1, wherein the second wall comprises a plurality of stiffening ribs disposed along the exterior surface of the second wall, the plurality of stiffening ribs extending radially outward from the inlet/outlet port to the annular stiffening lip.

* * * * *